(12) United States Patent
Kertser et al.

(10) Patent No.: US 11,052,212 B2
(45) Date of Patent: Jul. 6, 2021

(54) CAPNOXYGEN MASKS

(71) Applicant: ORIDION MEDICAL 1987 LTD., Jerusalem (IL)

(72) Inventors: Michael Kertser, Jerusalem (IL); Ibrahim Emtanis Abu Ali, Nazareth (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 486 days.

(21) Appl. No.: 15/874,055

(22) Filed: Jan. 18, 2018

(65) Prior Publication Data

US 2018/0207386 A1 Jul. 26, 2018

Related U.S. Application Data

(60) Provisional application No. 62/448,468, filed on Jan. 20, 2017.

(51) Int. Cl.
*A61M 16/08* (2006.01)
*A61B 5/097* (2006.01)
(Continued)

(52) U.S. Cl.
CPC ......... *A61M 16/085* (2014.02); *A61B 5/0075* (2013.01); *A61B 5/0205* (2013.01); *A61B 5/0836* (2013.01); *A61B 5/097* (2013.01); *A61B 5/682* (2013.01); *A61B 5/6838* (2013.01); *A61B 5/7242* (2013.01); *A61M 16/06* (2013.01); *A61M 16/0666* (2013.01); *A61M 16/0683* (2013.01); *A61M 16/0833* (2014.02); *G01N 33/497* (2013.01); *A61B 5/02416* (2013.01); *A61B 5/082* (2013.01); *A61B 5/0816* (2013.01); *A61B 5/6831* (2013.01); *A61B 2562/0204* (2013.01); *A61M 2202/0208* (2013.01);
(Continued)

(58) Field of Classification Search
CPC ................ A61M 16/085; A61M 16/06; A61M 16/0833; A61M 16/0666
See application file for complete search history.

(56) References Cited

U.S. PATENT DOCUMENTS 8,651,106 B1 * 2/2014 Morgan, Jr. ........... A62B 23/06
128/205.27
2002/0055685 A1 * 5/2002 Levitsky ........... A61M 16/0666
600/543
(Continued)

FOREIGN PATENT DOCUMENTS

EP 2204206 A1 7/2010
EP 2275031 A1 1/2011
(Continued)

OTHER PUBLICATIONS

International Search Report and Written Opinion for PCT Application No. PCT/IL2018/050068 dated Jun. 20, 2018; 17 pgs.

*Primary Examiner* — Margaret M Luarca
(74) *Attorney, Agent, or Firm* — Cantor Colburn LLP

(57) ABSTRACT

An oxygen mask configured for CO2 sampling and oxygen delivery, the oxygen mask having an oxygen inlet, a nasal breath-sampling element and a breath sampling port configured to receive breath samples, sampled by the breath-sampling element, wherein the breath-sampling element is configured to reduce dilution of exhaled breath by the delivered oxygen.

7 Claims, 11 Drawing Sheets

(51) Int. Cl.
    *A61M 16/06*    (2006.01)
    *A61B 5/00*     (2006.01)
    *A61B 5/083*    (2006.01)
    *A61B 5/0205*   (2006.01)
    *G01N 33/497*   (2006.01)
    *A61B 5/024*    (2006.01)
    *A61B 5/08*     (2006.01)
    *G01F 1/00*     (2006.01)

(52) U.S. Cl.
    CPC ............... *A61M 2202/0225* (2013.01); *A61M 2230/432* (2013.01); *G01F 1/00* (2013.01)

(56) References Cited

U.S. PATENT DOCUMENTS

| | | |
|---|---|---|
| 2008/0319334 A1 | 12/2008 | Yamamori |
| 2011/0240035 A1* | 10/2011 | Gillies .............. A61M 16/0666 128/207.18 |
| 2012/0167892 A1* | 7/2012 | Matula, Jr. ............ A61M 16/06 128/206.21 |
| 2012/0285448 A1 | 11/2012 | Dugan et al. |
| 2012/0289851 A1* | 11/2012 | Varga ................... A61B 5/0836 600/532 |
| 2014/0018691 A1* | 1/2014 | McNeill .............. A61M 16/085 600/532 |
| 2017/0007795 A1* | 1/2017 | Pedro ................ A61M 16/0672 |

FOREIGN PATENT DOCUMENTS

| | | |
|---|---|---|
| WO | 9733641 A1 | 9/1997 |
| WO | 2006039788 A1 | 4/2006 |
| WO | 2011030250 A1 | 3/2011 |
| WO | 2012094730 A1 | 7/2012 |
| WO | 2015119866 A1 | 8/2015 |
| WO | 2018029689 A1 | 2/2018 |

* cited by examiner

CAPNOXYGEN MASKS

This application claims the benefit of U.S. Provisional Application Ser. No. 62/448,468 filed Jan. 20, 2017, the content of which is incorporated herein by reference in its entirety for all purposes.

TECHNICAL FIELD

The present disclosure generally relates to the field of breath monitoring, specifically to $CO_2$ sampling alongside oxygen delivery.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The body needs oxygen to function properly and receives oxygen via the lungs to be metabolized in all cells of the body. Conditions affecting the lungs, such as chronic obstructive pulmonary disease (COPD), require oxygen therapy to get adequate oxygenation.

Nasal cannulas are capable of delivering oxygen at relatively low concentrations (typically between 24 to 40%) and at a relatively low flow rates (6 LPM). Nasal cannulas are, therefore, most often only suitable for patients with rather minor breathing problems. Oxygen masks, on the other hand, are capable of delivering oxygen at higher concentrations (40 to 60%) at relatively high flow rates between (10 to 15 LPM) and are, therefore, more suitable for patients with more severe breathing problems.

SUMMARY

Oxygen masks are often incompatible with $CO_2$ sampling primarily due to dilution of the breath sample by delivered oxygen, and due to rebreathing.

Advantageously, the capnoxygen masks disclosed herein are configured to provide high quality $CO_2$ monitoring alongside delivery of oxygen at high flow rates and concentrations.

According to some embodiments, there is provided a double-layered capnoxygen mask having a first compartment configured to receive high concentrations of oxygen for delivery to a patient and a second compartment configured for $CO_2$ sampling.

Advantageously, the double compartment capnoxygen mask provides comfortable wearing, reduced rebreathing, and oxygen delivery at high flow rates, along with high quality $CO_2$ monitoring. This is achieved by forming a sampling compartment in part of the mask closest to the patient, the sampling compartment designated to enable non-diluted $CO_2$ sampling. The outer compartment of the double compartment capnoxygen mask receives oxygen for delivery to the patient and is also referred to herein as the oxygen compartment.

According to some embodiments, the wall separating the compartments may include a plurality of perforations, optionally distributed throughout the wall surface, through which oxygen can reach the internal compartment. Advantageously, the perforations enable delivery of oxygen from multiple directions and facilitate dispersed rather than jet flow delivery of oxygen, thereby reducing rebreathing.

According to some embodiments, there is provided a capnoxygen mask including nasal prongs, through which exhaled air may be sampled. Advantageously, the nasal prongs are configured to provide high quality $CO_2$ monitoring alongside oxygen delivery at high flow rates and concentrations.

According to some embodiments, the nasal prongs may be semi-rigid nasal prongs fitted to be in front of the nasal openings. According to some embodiments, the capnoxygen mask may further include a sampling port, for example, on the nose-bridge outside the mask. The sampling port may be connected to the nasal prongs, thereby allowing direct and efficient transfer of exhaled breath outside the mask, while minimally interfering with patient comfort. According to some embodiments, the nasal prongs may be attached to external adjustment handles configured to enable adjustment of the nasal prongs' position. Advantageously, the adjustment handles may ensure optimal $CO_2$ monitoring and patient comfort for subjects with varying facial proportions.

According to some embodiments, there is provided a capnoxygen mask including a nasal trap, through which exhaled air may be sampled. The nasal trap is configured to ensure high quality $CO_2$ monitoring alongside oxygen delivery at high flow rates and concentrations. This is achieved by physical separation of the breath sampling area from the oxygen delivered.

According to some embodiments, the capnoxygen mask may include a manifold structure including an oxygen inlet, a sampling port, and a sampling tubing directly connected to the nasal trap. Advantageously, the manifold structure may be configured to enable oxygen, delivered through the oxygen inlet, to be dispersed within the manifold structure, thereby ensuring an essentially equal distribution of the oxygen throughout the mask.

According to some embodiments, there is provided a breath sampling cannula, including two sampling tubes, each configured for insertion into a subject's nostril. Advantageously, the sampling tubes include magnets, which are sufficiently strong to keep the cannula attached to/clipped on the subject's nose septum, while causing minimal interference with patient comfort. The breath sampling cannula is advantageously aligned with the patient's nose thereby reducing dilution as well as increasing patient comfort when worn in conjunction with oxygen masks.

According to some embodiments, there is provided a capnoxygen mask configured for $CO_2$ sampling and oxygen delivery, the capnoxygen mask having an oxygen inlet, a nasal breath-sampling element configured to reduce dilution of exhaled breath by the delivered oxygen, and a breath sampling port configured to receive breath samples, sampled by the breath-sampling element.

According to some embodiments, the nasal breath-sampling element may be molded on or otherwise attached to an internal side of the capnoxygen mask.

According to some embodiments, the capnoxygen mask may further include an oral sampling element configured for sampling exhaled breath from a subject's mouth, when in use.

According to some embodiments, the nasal breath-sampling element may be or may include two nasal prongs fitted within the mask so as to be positioned within or below a subject's nostrils, when in use. According to some embodiments, the two nasal prongs may be connected to an adjustment handle, the adjustment handle located outside the capnoxygen mask. According to some embodiments, movement of the adjustment handle may enable adjusting a position of the two nasal prongs within the capnoxygen mask.

According to some embodiments, the nasal breath-sampling element may be or may include a nasal trap. The nasal trap may be shaped to isolate a subject's nasal exhale area from oxygen delivered to the capnoxygen mask. According to some embodiments, the sampling port may be in fluid flow connection with the nasal trap.

According to some embodiments, the capnoxygen mask may further include a manifold structure, including the oxygen inlet and the breath sampling port. According to some embodiments, oxygen delivered through the oxygen inlet may be dispersed within the manifold. According to some embodiments, oxygen dispersed within the manifold may reach an area of the capnoxygen mask surrounding the nasal trap. According to some embodiments, the nasal trap may include a plurality of oxygen supply perforations configured to allow oxygen dispersed by the manifold structure to enter the nasal trap.

According to some embodiments, the nasal breath-sampling element may be or include an inner sampling compartment. According to some embodiments, the capnoxygen mask may include an inner wall separating the capnoxygen mask into an inner sampling compartment and an outer oxygen delivery compartment. According to some embodiments, the wall may include a plurality of oxygen supply perforations through which oxygen can reach the inner sampling compartment. According to some embodiments, the inner sampling compartment may include two nasal prongs fitted within the inner sampling compartment so as to be positioned within or below a subject's nostrils, when in use.

According to some embodiments, the capnoxygen mask may further include a breath sampling tube attached to the breath sampling port.

According to some embodiments, there is provided a breath sampling cannula having a first nasal prong and a first tube; the first tube being in fluid flow communication with the first nasal prong; and a second nasal prong and a second tube, the second tube being in fluid flow communication with the second nasal prong. According to some embodiments, the first tube and/or first nasal prong may include a first magnet and the second tube and/or second nasal prong may include a second magnet. According to some embodiments, the magnetic force between the first and second magnets enables grasping a nose septum on opposite sides thereof.

According to some embodiments, the first and second magnets comprise rare-earth magnets. According to some embodiments, the first and second magnets may be or may include neodymium magnets.

According to some embodiments, the breath sampling cannula may further include a sampling tube and a Y-junction interconnecting the first tube, the second tube and the sampling tube. According to some embodiments, the Y-junction may be sized and shaped to be pulled through a dedicated hole of an oxygen mask.

According to some embodiments, there is provided a capnoxygen system including: a breath sampling cannula having a first nasal prong and a first tube, the first tube being in fluid flow communication with the first nasal prong; a second nasal prong and a second tube, the second tube being in fluid flow communication with the second nasal prong; and a Y-junction interconnecting the first tube and the second tube with a breath sampling line. According to some embodiments, the first tube and/or first nasal prong may include a first magnet and the second tube and/or second nasal prong may include a second magnet. According to some embodiments, the magnetic force between the first and second magnets enables grasping a nose septum on opposite sides thereof. According to some embodiments, the capnoxygen system further includes an oxygen mask having an aperture configured to receive the Y-junction.

According to some embodiments, the first and second magnets may be or may include rare-earth magnets.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1A:
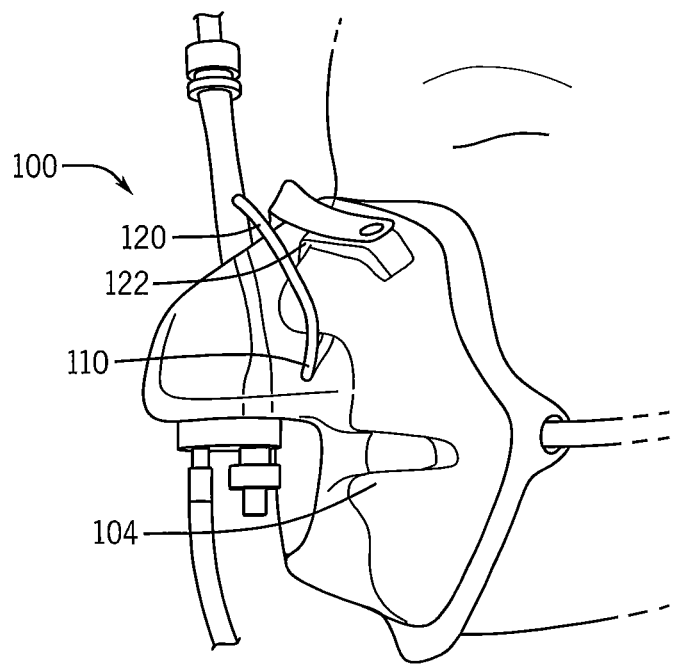
FIG. 1A shows a side view of a capnoxygen mask with nasal prongs, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. Additionally, it is to be explicitly understood that any combination of any one or more of the disclosed embodiments may be applicable and is within the scope of the disclosure.

The present disclosure generally relates to the field of breath monitoring, specifically to $CO_2$ sampling alongside oxygen delivery using oxygen masks.

According to some embodiments, there is provided a capnoxygen mask configured for $CO_2$ sampling, while at the same time administering oxygen. The capnoxygen mask includes an oxygen inlet, a nasal breath-sampling element and a breath sampling port configured to receive breath samples sampled by the breath-sampling element, wherein the breath-sampling element is configured to reduce dilution of exhaled breath by the delivered oxygen.

As used herein, the term "capnoxygen mask" may refer to a mask configured to provide oxygen to a subject, while allowing efficient and medically significant sampling of the exhaled carbon dioxide. According to some embodiments, the capnoxygen mask may cover the nose and mouth (oral nasal mask) or the entire face (full-face mask). The mask may be made of plastic, silicone, rubber or any other suitable material. According to some embodiments, the capnoxygen mask may be a non-rebreather mask having an attached reservoir bag, that connects to an external oxygen tank or bulk oxygen Supply system.

As used herein, the term "breath-sampling element" may refer to any element configured to facilitate measuring $CO_2$ concentrations in a patient's breath in a sufficiently reliably manner to obtain a satisfying waveform shape. Various breath-sampling elements may be envisaged, as further disclosed herein. According to some embodiments, the breath-sampling element may be an integral part of the capnoxygen mask. For example, the breath-sampling element may be molded with or otherwise attached to an inner side of the capnoxygen mask, i.e., the side of the capnoxygen mask facing the patient. Alternatively, the breath-sampling element may be a separate element configured to be incorporated and/or attached to existing oxygen masks as a modular element, so as to form an integral unit therewith.

As used herein, the term "reduced dilution" with regards to the breath-sampling element, may refer to the breath-sampling element being and/or having structural features, which sufficiently prevent dilution of the subject's exhaled breath to obtain a satisfying waveform.

As used herein the term "satisfying waveform" may refer to a waveform having a less than 10%, less than 5%, less than 1% deviation from the waveform which would have been obtained would the breath sampling be entirely undiluted by delivered oxygen. Each possibility is a separate embodiment.

As used herein, the terms "subject" and "patient" may be used interchangeably and may refer to any individual undergoing $CO_2$ monitoring during oxygen delivery, using oxygen delivery masks.

According to some embodiments, the capnoxygen mask may further include an oral sampling element, such as, but not limited to, an oral prong, configured for sampling from a subject's mouth, when in use.

According to some embodiments, the capnoxygen mask may further include a breath sampling tube attached to and/or attachable to the breath sampling port. Additionally or alternatively, the breath sampling port may include a connector configured for connection to a breath sampling tube.

According to some embodiments, the breath sampling port may be positioned on a nose-bridge outside of the capnoxygen mask. According to some embodiments, the breath sampling port may be positioned on part of the mask being beneath and/or in front of the subject's nose, mouth or cheek, when in use. Each possibility is a separate embodiment.

According to some embodiments, the nasal breath-sampling element may be and/or may include two nasal prongs fitted within the mask so as to be positioned within or below a subject's nostrils, when in use. According to some embodiments, the nasal prongs may be an integral part of the capnoxygen mask, e.g. molded with the mask. Alternatively, the oral prongs may be attached to the capnoxygen mask, or parts thereof, so as to form an integral part therewith. This advantageously provides a single integrated unit, which is much more comfortable to wear than the bulky simultaneous wearing of an oxygen mask for oxygen delivery and a stand-alone breath sampling cannula for breath monitoring.

According to some embodiments, the nasal prongs may be connected to an adjustment handle, located outside the oxygen mask and enabling adjustment of the position of the nasal prongs within the oxygen mask. According to some embodiments, the adjustment handle may be configured to adjust the distance between the nasal prongs. Additionally or alternatively, the adjustment handle may be configured to adjust the angle of the nasal prongs relative to the capnoxygen mask. Additionally or alternatively, the adjustment handle may be configured to adjust the distance between the nasal prongs and the subject's nostrils and thus the depth of their insertion into the subject's nostrils.

According to some embodiments, the nasal breath-sampling element may be or may include a nasal trap, shaped to fit around a subject's nose. The nasal trap may thus isolate the subject's nasal exhale area from oxygen delivered to the capnoxygen mask. According to some embodiments, the sampling port may be in fluid flow connection with the nasal trap. According to some embodiments, the nasal trap may be directly connected to the sampling port.

According to some embodiments, the nasal trap may include a plurality of oxygen supply perforations through which oxygen may enter the nasal trap. As used herein, the term "plurality", when referring to oxygen supply perforations, may include more than 5 oxygen supply perforations, more than 10 oxygen supply perforations, more than 20 oxygen supply perforations, or any other suitable number of oxygen supply perforations. Each possibility is a separate embodiment. According to some embodiments, the plurality of oxygen supply perforations may be dispersed throughout the surface of the nasal trap, such that the delivered oxygen enters the nasal trap from multiple directions. Advantageously, the perforations generate dispersed rather than jet flow oxygen delivery, thereby reducing dilution of the sampled exhaled breath by the delivered oxygen as well as rebreathing.

Additionally or alternatively the capnoxygen mask may include a manifold structure including the oxygen inlet and the breath sampling port. According to some embodiments, the manifold structure may include a sampling tubing connecting the nasal trap to the breath sampling port. According to some embodiments, oxygen delivered through the oxygen inlet may be dispersed within the manifold structure and around the sampling tubing. From the manifold structure, the oxygen may be delivered to the nasal trap at a dispersed rather than jet flow, thereby reducing dilution of the sampled exhaled breath by the delivered oxygen as well as rebreathing.

According to some embodiments, the capnoxygen mask may be a double layered capnoxygen mask. According to some embodiments, the capnoxygen mask may include a wall inside the mask, generating an inner lumen/compartment configured for sampling, also referred to herein as a "sampling compartment", and an outer oxygen delivery lumen/compartment, also referred to herein as an "oxygen compartment". According to some embodiments, the wall may include a plurality of oxygen supply perforations through which oxygen can reach the inner sampling compartment. Advantageously, the perforations generate dispersed rather than jet flow oxygen delivery, thereby reducing dilution of the sampled exhaled breath by the delivered oxygen as well as rebreathing.

According to some embodiments, the sampling compartment may include nasal prongs (e.g. two nasal prongs) fitted within the inner sampling compartment so as to be positioned within or below a subject's nostrils when in use, as essentially described herein.

According to some embodiments, there is provided a breath sampling cannula including a first nasal prong and a first tube, the first tube being in fluid flow communication with the first nasal prong; a second nasal prong and a second tube the second tube being in fluid flow communication with the second nasal prong; wherein the first tube includes a first magnet and the second tube includes a second magnet, and wherein a magnetic force between the first and the second magnets enables grasping a subject's nose septum on opposite sides thereof, when in use.

According to some embodiments, the (first and/or second) nasal prong and the (first and/or second) tubes may be coextensive, and the nasal prong may refer to and/or include the part of the tube which is inserted into the patient's nostrils and/or the part of the tube (the distal end thereof) proximate to the subject's nostrils, when in use. Alternatively, the nasal prong may be a separate element and may have a smaller diameter than the tube, in which case the nasal prong is molded on/with or otherwise attached to the tube, so as to be in fluid communication therewith.

According to some embodiments, the breath sampling cannula may further include a breath sampling tube and a Y-junction, the Y-junction interconnecting the first tube, the second tube and the breath sampling tube, such that exhaled breath can flow from the first and second tubes to the breath sampling tube, and from there to the monitor (e.g. a capnography).

According to some embodiments, the breath sampling cannula may advantageously be devoid of attachment means (such as straps configured to be worn around the subject's ears) and may thus be worn in conjunction with an oxygen mask without causing patient discomfort. According to some embodiments, the Y-junction may be sized and shaped to be pulled through a hole of an oxygen mask.

According to some embodiments, the magnets may be sufficiently strong to keep the cannula attached to/clipped on the subject's nose septum, without interfering with patient comfort. According to some embodiments, the magnets may be or may include rare-earth magnets. According to some embodiments, the rare-earth magnets may be or may include neodymium magnets (e g. neodymium balls 4-5 mm). According to some embodiments, the rare-earth magnets may be or may include samarium-cobalt magnets. According to some embodiments, the magnets may be or may include ferrite or ceramic magnets. According to some embodiments, the magnets may produce a magnetic field, which exceeds 1.2 tesla, 1.25 tesla, 1.3 tesla, 1.4 tesla or 1.5 tesla. Each possibility is a separate embodiment. According to some embodiments, the magnets may be coated or may be a material suitable to provide protection and/or reduce the vulnerability of the magnets.

Examples illustrative of embodiments are described below with reference to figures attached hereto. Combinations of the below embodiments are envisaged and are within the scope of this disclosure. For example, certain elements described/depicted in one embodiment/figure, e.g. nasal prongs, may be included in other figures, despite not being depicted.

Figure 1B:
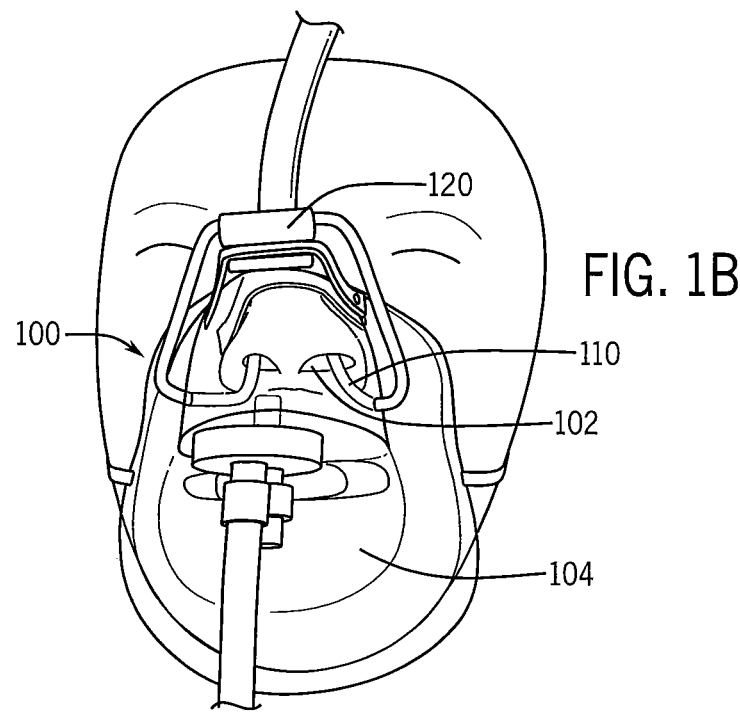
FIG. 1B shows a front view of a capnoxygen mask with nasal prongs, according to some embodiments.

Reference is now made to FIG. 1A and FIG. 1B, which show side and front views of a capnoxygen mask 100 with nasal prongs 110, according to some embodiments. Nasal prongs 110 may be semi-rigid and arranged to be in front of a subject's nasal openings 102. Nasal prongs 110 are externally connected to a sampling port 120, here positioned on a nose-bridge 122 outside of the capnoxygen mask 100; however, alternative positioning of the sampling port is also envisaged, as further elaborated herein, and is thus within the scope of the disclosure. The capnoxygen mask 100 may optionally further include an oral sampling port (not shown) configured for sampling from the subject's mouth 104.

Figure 2:
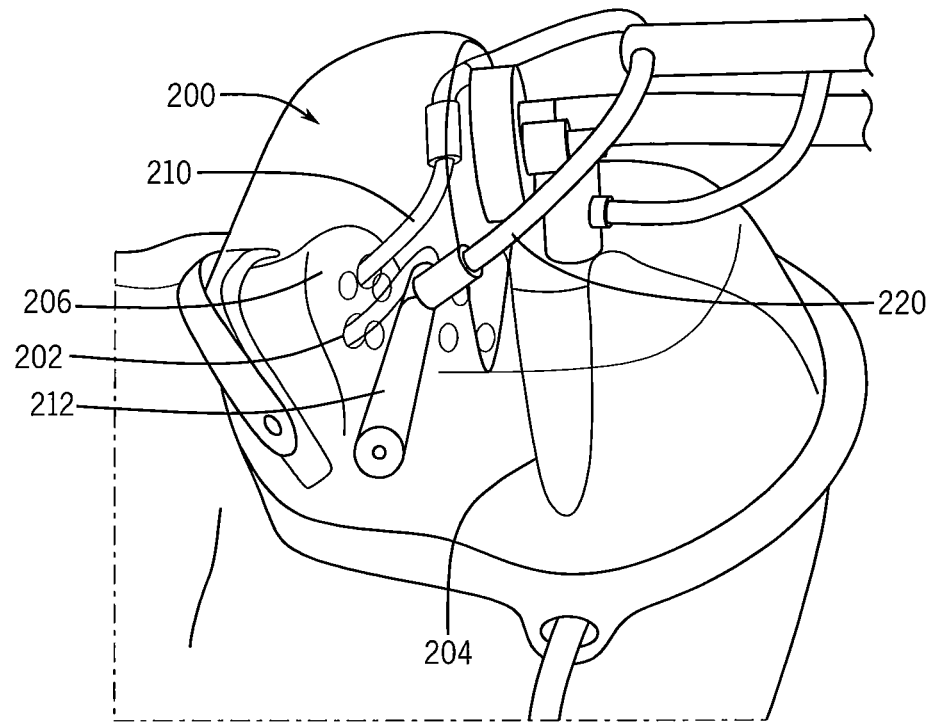
FIG. 2 shows a side view of a capnoxygen mask with nasal prongs and adjustment handles, according to some embodiments.

Reference is now made to FIG. 2, which shows a side views of a capnoxygen mask 200 with nasal prongs 210 and adjustment handles 212, according to some embodiments. Adjustment handles 212 are configured to adjust the position of nasal prongs 210 so as to ensure optimal $CO_2$ monitoring and patient comfort in subjects with varying facial proportions. Nasal prongs 210 are essentially similar to nasal prongs 110 and may be semi-rigid and arranged to be in front of a subject's nasal openings 202. Nasal prongs 210 are externally connected to a sampling port 220, here positioned below the subject's nose 206 outside the capnoxygen mask 200; however, alternative positioning of the sampling port is also envisaged, as further elaborated herein, and is thus within the scope of the disclosure. The capnoxygen mask 200 may optionally further include an oral sampling port (not shown) configured for sampling from the subject's mouth 204.

Figure 3:
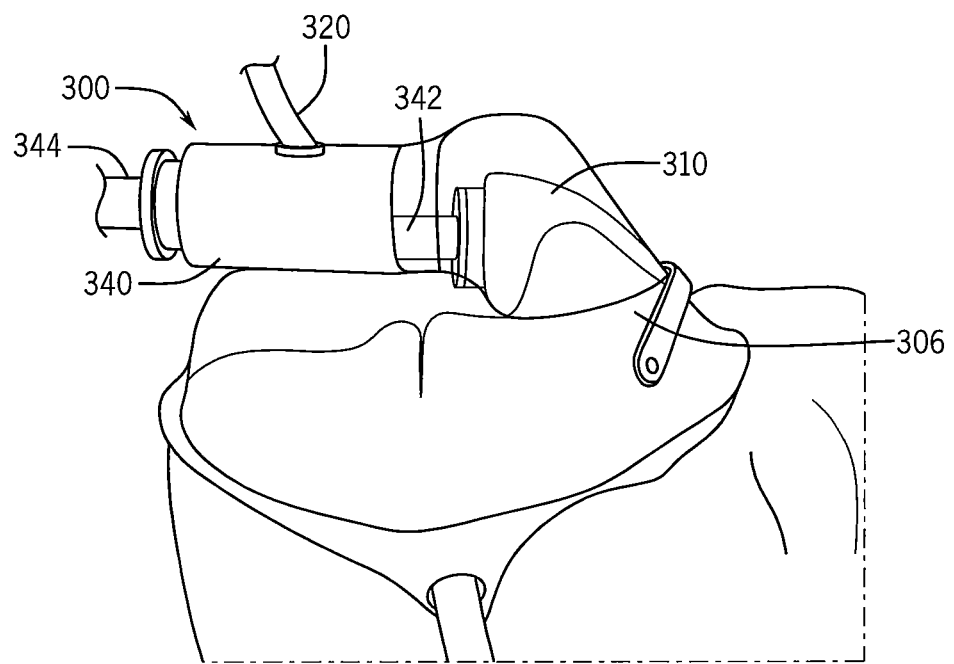
FIG. 3 shows a side view of a capnoxygen mask with nasal trap, according to some embodiments.

Reference is now made to FIG. 3, which shows a side view of a capnoxygen mask 300 with nasal trap 310, according to some embodiments. Nasal trap 310 is optionally adjustable and is configured to fit the patient's face geometry so as to surround the patient's nose 306. As a result, an isolated breath sampling area is formed around nose 306, which prevents dilution of exhaled breath by delivered oxygen. The capnoxygen mask 300 further includes a manifold structure 340 including a sampling port 320, sampling tubing 342, configured to connect the nasal trap 310 to sampling port 320, and an oxygen inlet 344. Oxygen, delivered through the oxygen inlet 344, is dispersed within manifold structure 340 around the sampling tubing 342. From manifold structure 340, oxygen may be delivered to the nasal trap 310 at a dispersed flow rather than a jet flow, thereby reducing rebreathing as well as dilution of the sampled exhaled breath by the delivered oxygen.

Figure 4A:
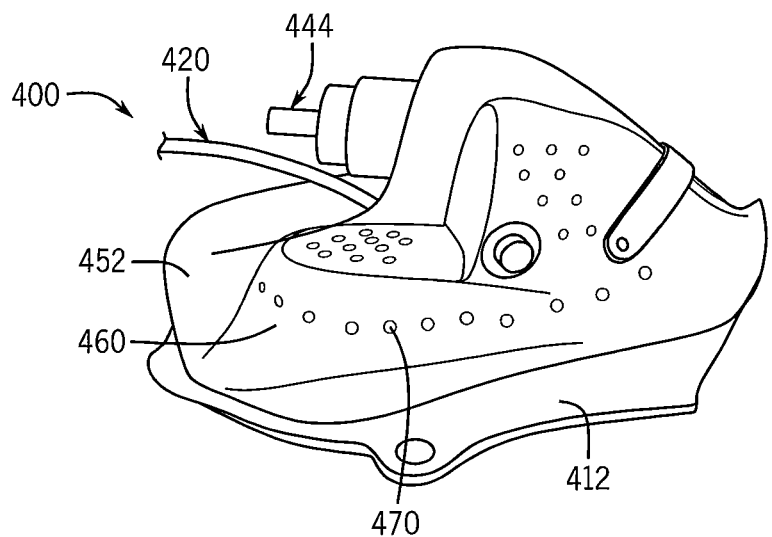
FIG. 4A shows a side view of a double layered capnoxygen mask, according to some embodiments.
Figure 4B:
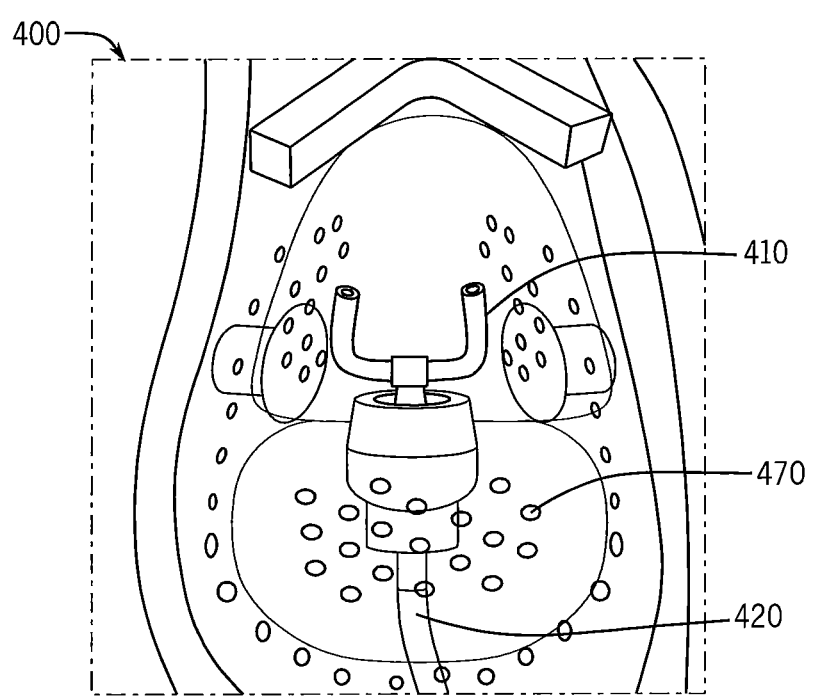
FIG. 4B, shows a double layered capnoxygen mask viewed from the inside, according to some embodiments.

Reference is now made to FIG. 4A and FIG. 4B, which show a double layered capnoxygen mask 400, according to some embodiments. The double layered capnoxygen mask 400 generates a double compartment mask, including a first inner compartment 412 (closest to the patient, when worn) configured to enable non-diluted $CO_2$ sampling, and a second outer compartment 452 configured to receive oxygen from oxygen inlet 444. A wall 460 separating the first inner compartment 412 and the second outer compartment 452 includes a plurality of perforations 470, through which oxygen can reach first inner compartment 412. The perforations 470 may be positioned throughout the surface of the wall 460, thereby enabling delivery of oxygen from multiple directions and at a dispersed rather than jet flow. The first inner compartment 412 may further include nasal prongs 410 configured to further decrease the dilution of the patient's exhaled breath with the delivered oxygen. The nasal prongs 410 are connected to sampling port 420, as essentially described herein.

Figure 5A:
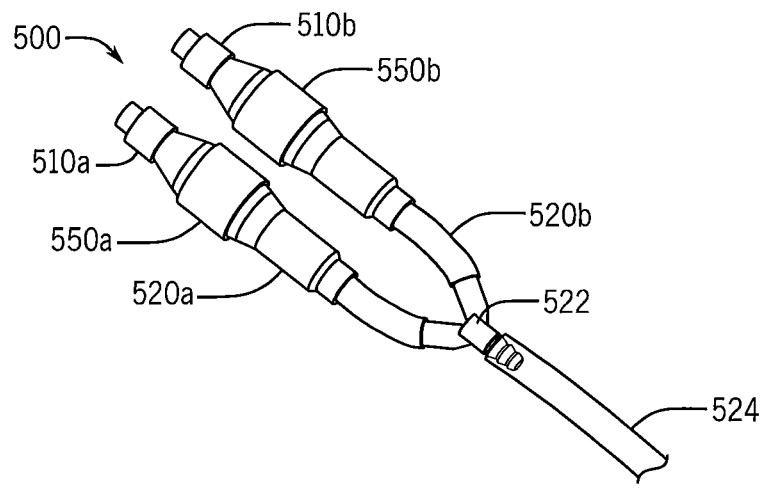
FIG. 5A shows a breath sampling cannula including magnets, according to some embodiments.
Figure 5B:
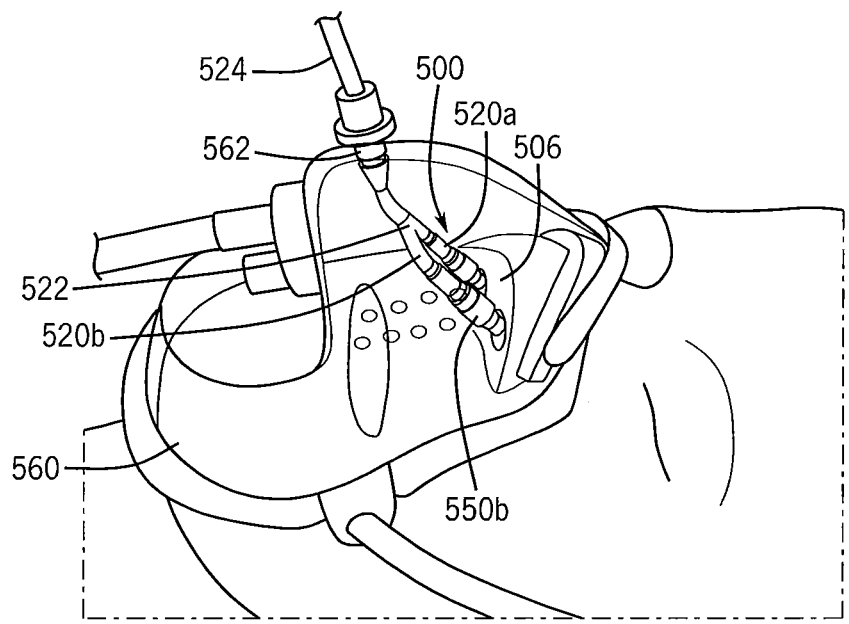
FIG. 5B shows the breath sampling cannula including magnets of FIG. 5A when used in conjunction with an oxygen mask, according to some embodiments.

Reference is now made to FIG. 5A and FIG. 5B, which show a breath sampling cannula 500 including magnets 550a and 550b, according to some embodiments. The breath sampling cannula 500 includes a first nasal prong 510a and a first tube 520a being in fluid flow communication, and a second nasal prong 510b and a second tube 520b being in fluid flow communication. The tubes 520a and 520b are further in fluid flow communication with a Y-junction 522 and a breath sampling tube 524, through which exhaled breath may reach the breath monitor (not shown). The magnet 550a is positioned on the nasal prong 510a and/or on the tube 520a, and the magnet 550b is positioned on the nasal prong 510b and/or on the second tube 520b, in such a manner that the magnetic force of the magnets 550a and 550b (e.g. neodymium rare magnets) causes the nasal prongs 510a and 510b and/or the tube 520a and the tube 520b to grasp the nose septum 506 on opposite sides thereof, when in use. The Y-junction 522 is sized and shaped to be pulled through a dedicated hole 562 of oxygen mask 560 (FIG. 5B), thereby facilitating efficient non-diluted $CO_2$ sampling alongside oxygen delivery, using any type of oxygen mask.

Examples

Test Setup on Manikin

Figure 6:
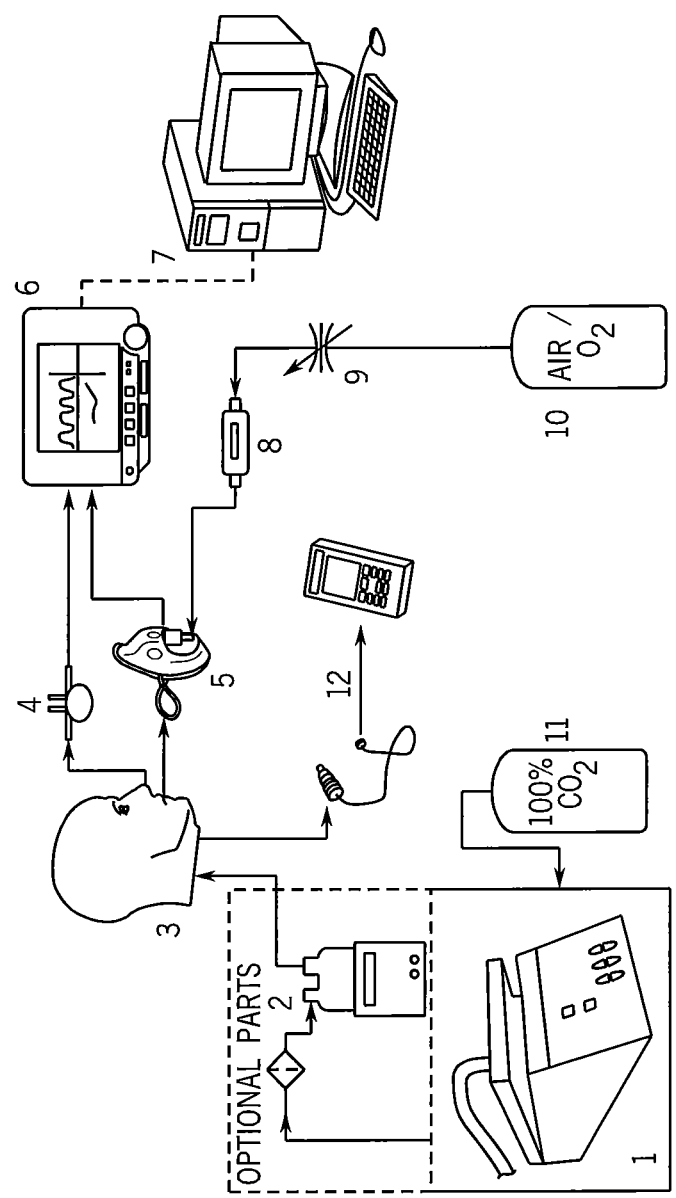
FIG. 6 shows an outline of the test setup used for evaluating the capnoxygen mask disclosed herein.

The test setup for the capnoxygen masks disclosed herein was built on the basis of the Ingmar Medical Breath Simulator with mechanical lung, connected to a manikin head, connected to a capnograph, measuring mask performance in terms of capnography within a defined set of breathing regimes and oxygen (air) flows. An outline of the test setup is shown in FIG. 6. Table 1 below specifies the elements of the system, as shown in FIG. 6.

TABLE 1

| Figure elements | |
|---|---|
| ## | Description |
| 1 | Laboratory Lung Model |
| 2 | Humidifier + filter (optional) |
| 3 | Manikin head |
| 4 | Standard Cannula (reference) |
| 5 | Oxygen Mask being tested |
| 6 | Capnograph |
| 7 | Computer |
| 8 | TSI Mass Flow Meter (up to 20 L/min) |
| 9 | Restrictor valve |
| 10 | Oxygen/Air gas reservoir |
| 11 | 100% $CO_2$, with calibrated flow |
| 12 | MiniOx 3000 oxygen meter (optional) |

The following settings were implemented:

Breath Mode="Eupnea" (Normal breathing)

Compliance=50 mL/cmH2O

Restriction=20 cmH2O/L/s (Restrictor used=Rp20)

Offset (AKA Dead Space)=140 ml

Inhalation/exhalation (I/E) ratio=1/2

Procedure:
1. The reference setup (baseline) measurement was performed with a nasal cannula (without mask) in order to calibrate the exhaled $CO_2$ gas to receive a 35 mmHg $CO_2$ partial pressure on nasal breathing.
2. The mask prototype was placed on the manikin head and the $EtCO_2$ signal was measured through the sampling port at varying oxygen/air flow rates (5 liters per minute (LPM) and 15 LPM), tidal volumes (250-700 mL) and respiration rates (10-25 breaths per minute (BPM)).
3. All results were recorded on a Capnostream20 capnograph.

In-Vivo Testing

The capnoxygen masks, disclosed herein, were tested in-vivo on a healthy test-subject, evaluating regular breathing at varying respiration rates and oxygen/air flow (nasal breathing). A metronome was used to guide the respiration rate during the measurement. All results were recorded on a Capnostream20 capnograph and appropriate waveforms recorded.

Test Results

POM M1 Oxygen Mask

Figure 7:
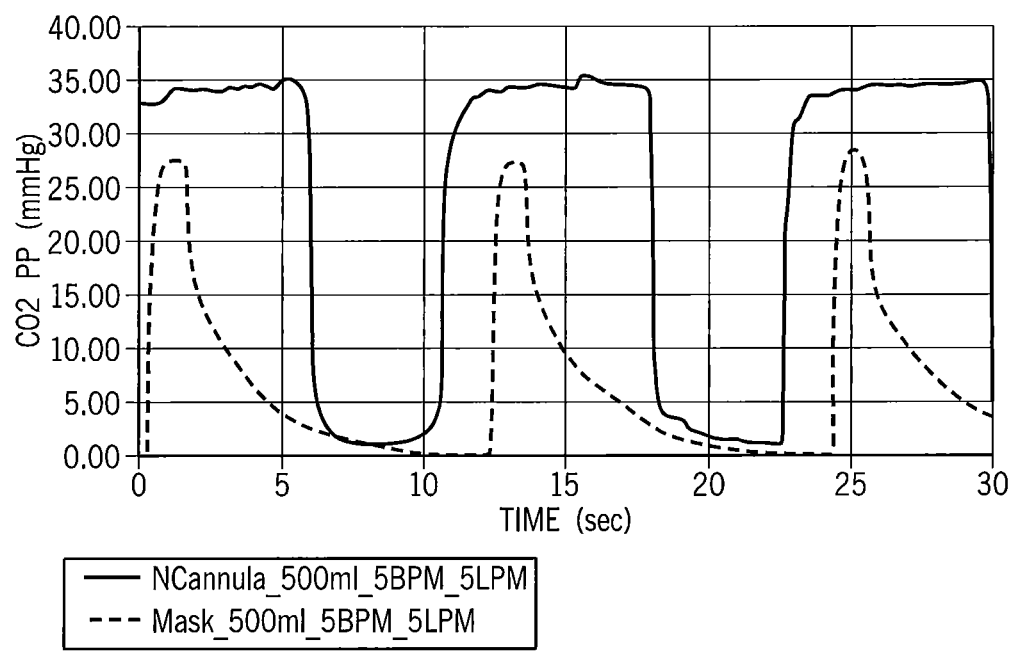
FIG. 7 shows the $CO_2$ waveforms obtained when evaluating a standard nasal cannula and oxygen delivery mask (POM M1)

FIG. 7 depicts the $CO_2$ waveforms obtained using the reference setup (nasal cannula) as compared to a standard oxygen delivery mask (POM M1) at 500 ml tidal volume, 5 BPM respiratory rate and 5 LPM oxygen flow. As seen from FIG. 7, using an oxygen mask causes dilution of the exhaled breath, and, as a result, negatively affects the obtained waveform.

Capnoxygen Mask with Nasal Prongs

The capnoxygen mask includes nasal prongs, fitted to be in front of a subject's nasal openings and externally connected to the sampling port on the nose-bridge outside of the mask, as shown in FIG. 1A and FIG. 1B.

Figure 8A:
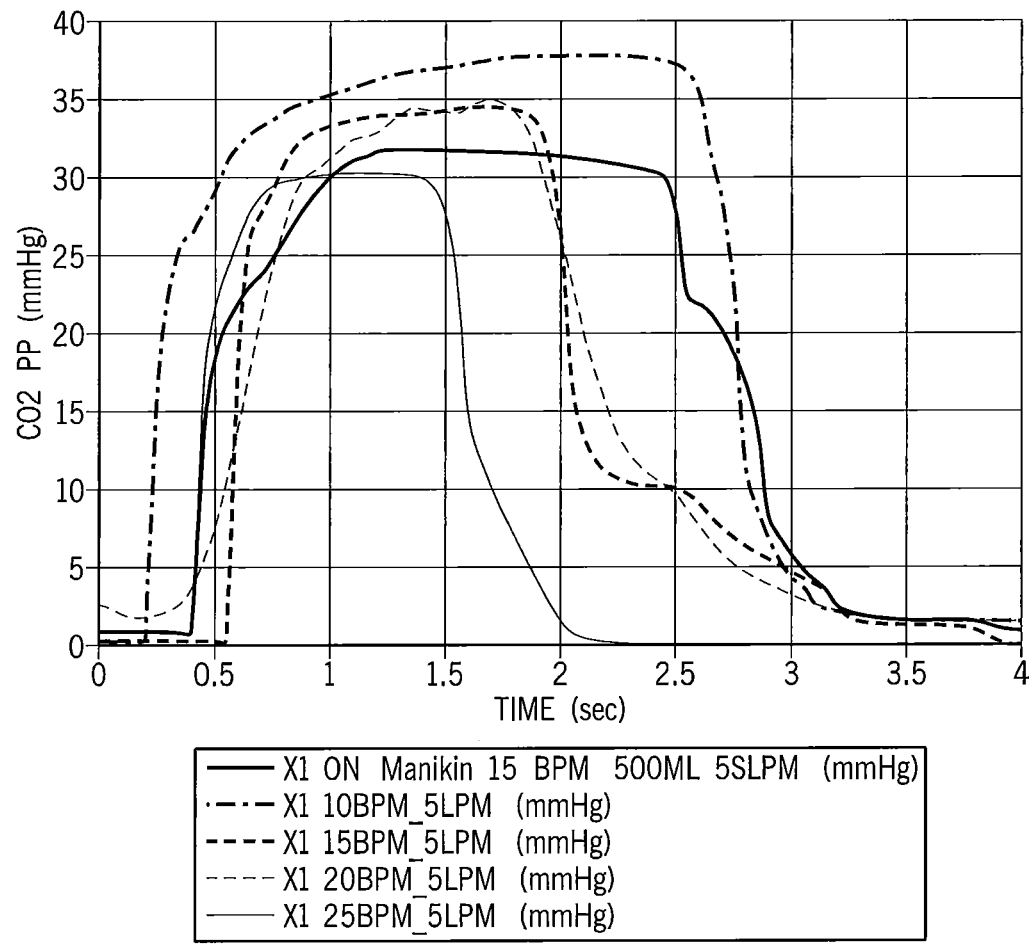
FIG. 8A shows the $CO_2$ waveforms obtained when evaluating the capnoxygen mask with nasal prongs depicted in FIG. 1A and FIG. 1B at a 5 LPM oxygen flow rate.
Figure 8B:
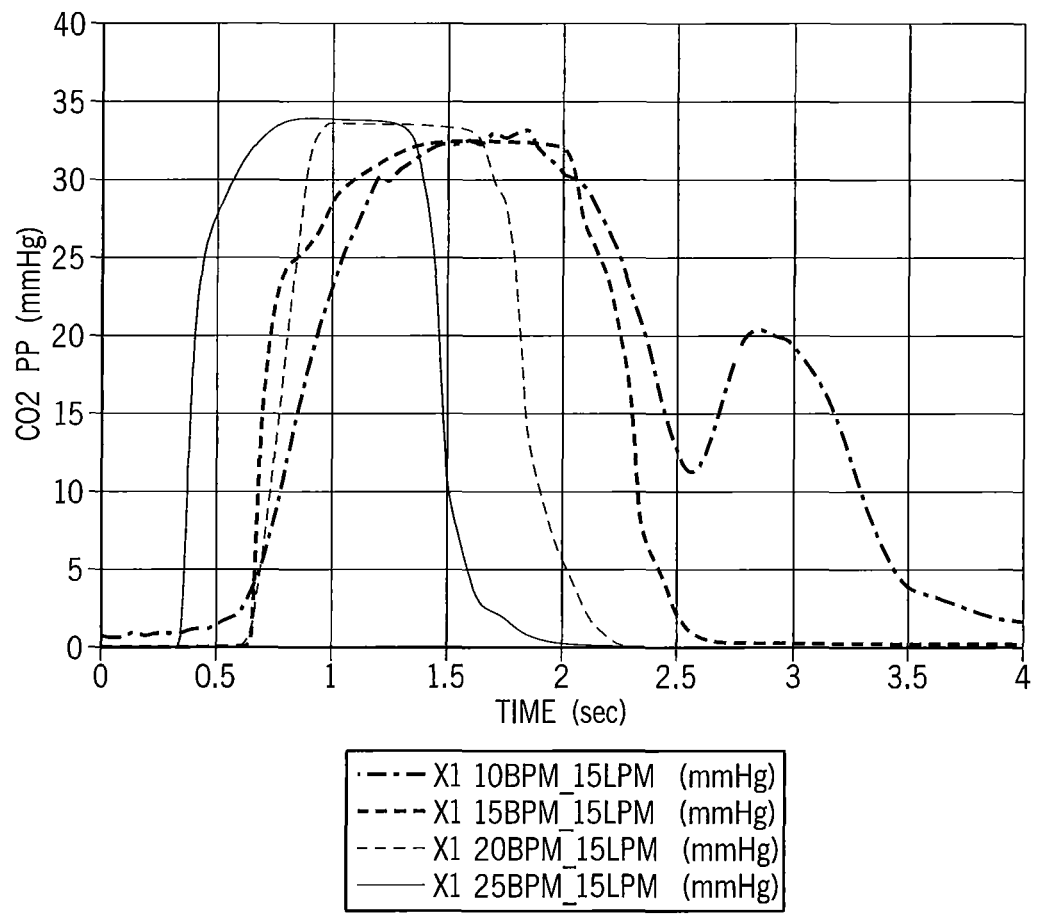
FIG. 8B shows the $CO_2$ waveforms obtained when evaluating the capnoxygen mask with nasal prongs depicted in FIG. 1A and FIG. 1B at a 15 LPM oxygen flow rate.

Measurement results, obtained when tested on a manikin according to the setup described above, are shown in Table 2 and Table 3 below, and the $CO_2$ waveform, derived from the measurements, is shown in FIG. 8A and FIG. 8B, solid black line.

TABLE 2

Partial pressure $CO_2$ (mmHg) at 5 L LPM oxygen flow.

| Tidal Volume (mL) | RR (BPM) | | | |
|---|---|---|---|---|
| | 10 | 15 | 20 | 25 |
| 700 | 29 | | | |
| 600 | 29 | 30 | 30 | |
| 500 | 29 | 29 | 30 | 31 |
| 450 | 29 | 29 | 30 | 31 |
| 400 | 29 | 28 | 29 | 30 |
| 350 | 29 | 29 | 29 | 30 |
| 300 | 29 | 29 | 29 | 30 |
| 250 | 32 | 29 | 30 | 31 |

TABLE 3

Partial pressure $CO_2$ (mmHg) at 15 L LPM oxygen flow

| Tidal Volume (mL) | RR (BPM) | | | |
|---|---|---|---|---|
| | 10 | 15 | 20 | 25 |
| 700 | 31 | | | |
| 600 | 32 | 32 | 35 | |
| 500 | 30 | 33 | 35 | 35 |
| 450 | 31 | 32 | 35 | 36 |
| 400 | 32 | 32 | 35 | 36 |
| 350 | 32 | 32 | 35 | 37 |
| 300 | 33 | 34 | 35 | 38 |
| 250 | 35 | 35 | 35 | 39 |

As seen from Tables 2 and 3, partial pressure $CO_2$ values were satisfyingly close to those obtained using the nasal cannula (35 mmHg) and are thus indicative of minimal dilution of the breath samples by the supplied oxygen, whether delivered at low (5 LPM) or high (15 LPM) flow.

Table 4 below provides the in-vivo (test subjects) results, and FIG. 8A and FIG. 8B provide the $CO_2$ waveforms obtained at 5 LPM and 15 LPM oxygen delivery, respectively.

TABLE 4

Partial pressure $CO_2$ (mmHg) at 5 and 15 L LPM oxygen flow.

| | Flow (LPM) | |
|---|---|---|
| RR (BPM) | 5 | 15 |
| 10 | 38 | 35 |
| 15 | 35 | 35 |
| 20 | 34 | 35 |
| 25 | 31 | 34 |

Surprisingly, the in-vivo measurement indicated an even lesser dilution than that obtained when performing the measurements on the manikin, probably due to inaccurate upper airway geometry and facial proportion of the manikin.

Capnoxygen Mask with Nasal Trap

The capnoxygen mask includes an internal adjustable nasal-add-on (nasal trap) which may be adjusted to fit patient geometry, as shown in FIG. 3.

Figure 9A:
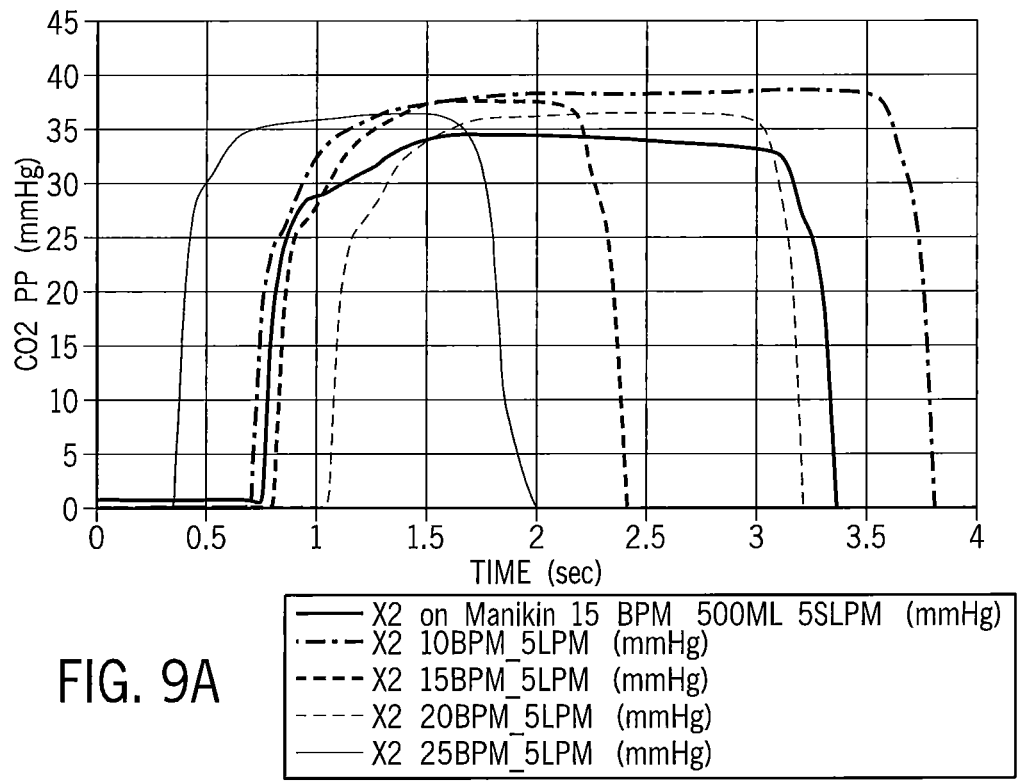
FIG. 9A shows the $CO_2$ waveforms obtained when evaluating the capnoxygen mask with nasal trap depicted in FIG. 3 at a 5 LPM oxygen flow rate.
Figure 9B:
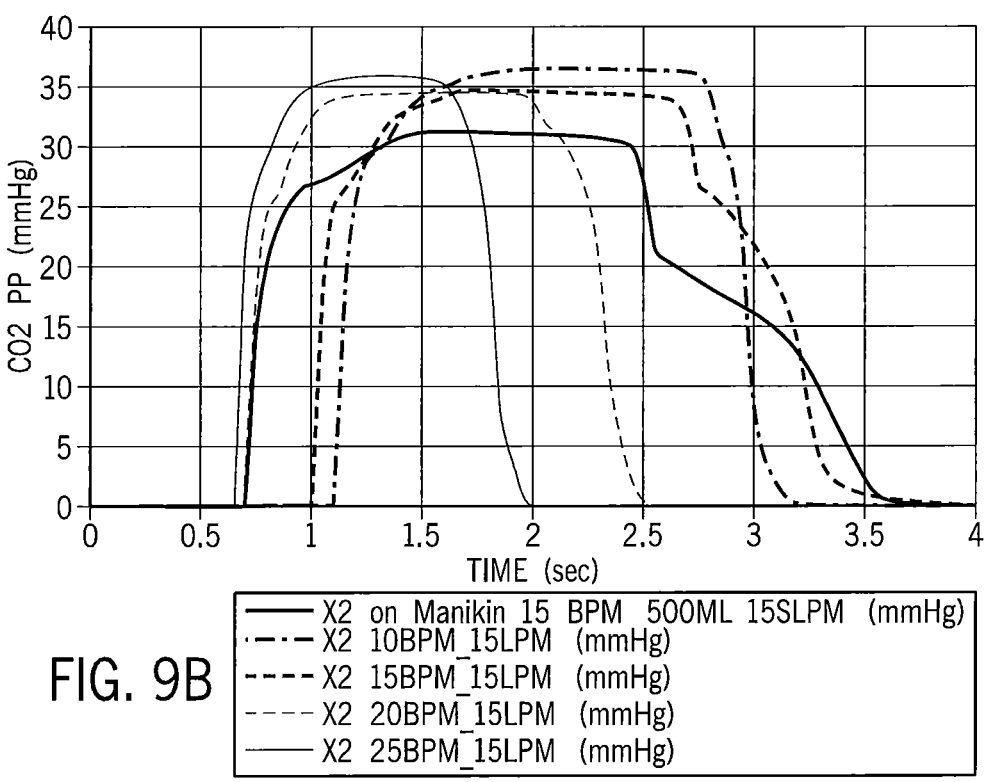
FIG. 9B shows the $CO_2$ waveforms obtained when evaluating the capnoxygen mask with nasal trap depicted in FIG. 3 at a 15 LPM oxygen delivery flow rate.

Measurement results, obtained when tested on a manikin according to the setup described above, are shown in Table 5 and Table 6 below, and the $CO_2$ waveforms derived from the measurements are shown in FIG. 9A and FIG. 9B, solid black line.

TABLE 5

Partial pressure $CO_2$ (mmHg) at 5 L LPM oxygen flow.

| Tidal Volume (mL) | RR (BPM) | | | |
|---|---|---|---|---|
| | 10 | 15 | 20 | 25 |
| 700 | 34 | | | |
| 600 | 34 | 34 | 35 | |
| 500 | 32 | 35 | 34 | 35 |
| 450 | 32 | 35 | 35 | 35 |
| 400 | 35 | 35 | 35 | 35 |
| 350 | 35 | 35 | 37 | 36 |
| 300 | 36 | 35 | 37 | 37 |
| 250 | 39 | 35 | 39 | 38 |

TABLE 6

Partial pressure $CO_2$ (mmHg) at 15 L LPM oxygen flow

| Tidal Volume (mL) | RR (BPM) | | | |
|---|---|---|---|---|
| | 10 | 15 | 20 | 25 |
| 700 | 32 | | | |
| 600 | 31 | 32 | 32 | |
| 500 | 32 | 32 | 32 | 35 |
| 450 | 32 | 32 | 33 | 35 |
| 400 | 33 | 33 | 34 | 35 |
| 350 | 33 | 33 | 34 | 35 |
| 300 | 34 | 35 | 37 | 37 |
| 250 | 35 | 37 | 36 | 37 |

As seen from Tables 5 and 6, partial pressure $CO_2$ values were satisfyingly close to those obtained using the nasal cannula (35 mmHg) and are thus indicative of minimal dilution of the breath samples by the supplied oxygen, whether delivered at low (5 LPM) or high (15 LPM) flow.

Table 7 below provides the in-vivo (test subjects) results, and FIG. 9A and FIG. 9B show the $CO_2$ waveforms obtained at 5 LPM and 15 LPM oxygen delivery, respectively.

TABLE 7

Partial pressure $CO_2$ (mmHg) at 5 and 15 L LPM oxygen flow.

| | Flow (LPM) | |
|---|---|---|
| RR (BPM) | 5 | 15 |
| 10 | 39 | 38 |
| 15 | 38 | 37 |
| 20 | 38 | 37 |
| 25 | 38 | 38 |

Surprisingly, the in-vivo measurement indicated an even lesser dilution than that obtained when performing the measurements on the manikin, probably due to inaccurate upper airway geometry and facial proportion of the manikin.

Double Layered Capnoxygen Mask

The double layered capnoxygen mask (shown in FIG. 4A and FIG. 4B) features a modified non-rebreather mask approach. The mask is double-layered, generating an internal space serving as an oxygen delivery manifold, configured to deliver a high concentration of $O_2$ to the patient from all-around the face.

Figure 10A:
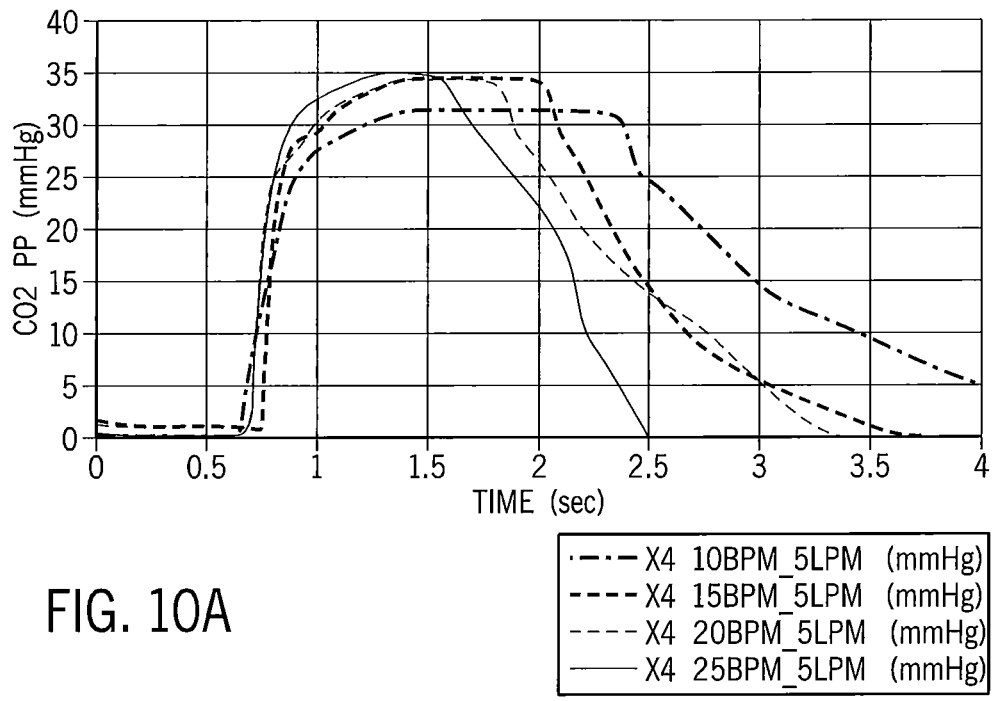
FIG. 10A shows the $CO_2$ waveforms obtained when evaluating the double layered capnoxygen mask depicted in FIG. 4A and FIG. 4B at a 5 LPM oxygen flow rate.
Figure 10B:
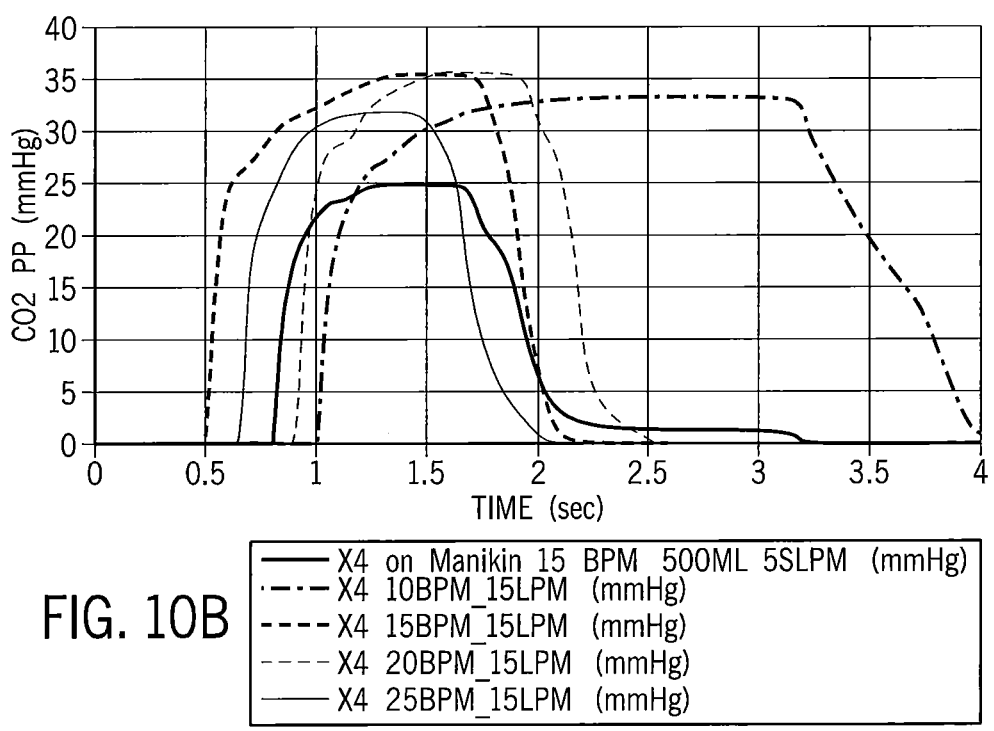
FIG. 10B shows the $CO_2$ waveforms obtained when evaluating the double layered capnoxygen mask depicted in FIG. 4A and FIG. 4B at a 15 LPM oxygen flow rate.

Measurement results, obtained when tested on a manikin according to the setup described above, are shown in Table 8 and Table 9 below, and the $CO_2$ waveforms, derived from the measurements is shown in FIGS. 10A and 10B, solid black line.

TABLE 8

Partial pressure $CO_2$ (mmHg) at 5 L LPM oxygen flow.

| Tidal Volume (mL) | RR (BPM) | | | |
|---|---|---|---|---|
| | 10 | 15 | 20 | 25 |
| 700 | 32 | | | |
| 600 | 30 | 32 | 33 | |
| 500 | 30 | 31 | 33 | 30 |
| 450 | 29 | 31 | 35 | 35 |
| 400 | 30 | 31 | 32 | 35 |
| 350 | 30 | 31 | 32 | 35 |
| 300 | 31 | 32 | 32 | 35 |
| 250 | 32 | 34 | 32 | 34 |

TABLE 9

Partial pressure $CO_2$ (mmHg) at 15 L LPM oxygen flow

| Tidal Volume (mL) | RR (BPM) | | | |
|---|---|---|---|---|
| | 10 | 15 | 20 | 25 |
| 700 | 25 | | | |
| 600 | 25 | 25 | 26 | |
| 500 | 25 | 25 | 25 | 26 |
| 450 | 25 | 25 | 25 | 26 |
| 400 | 25 | 25 | 25 | 27 |
| 350 | 26 | 25 | 25 | 27 |
| 300 | 25 | 25 | 25 | 28 |
| 250 | 25 | 25 | 24 | 27 |

As seen from Table 8, partial pressure $CO_2$ values were satisfyingly close to those obtained using the nasal cannula (35 mmHg) and are thus indicative of minimal dilution of the breath samples by the supplied oxygen when delivered at low (5 LPM). At the high (15 LPM) flow, the partial pressure values obtained indicated dilution of the exhaled breath by the delivered oxygen. This is probably due to the inaccurate upper airway geometry and facial proportion of the manikin.

Table 10 below provides the in-vivo (test subjects) results, and FIG. 10A and FIG. 10B show the $CO_2$ waveforms obtained at 5 LPM and 15 LPM oxygen delivery, respectively.

TABLE 10

Partial pressure $CO_2$ (mmHg) at 5 and 15 L LPM oxygen flow.

| RR (BPM) | Flow (LPM) | |
|---|---|---|
| | 5 | 15 |
| 10 | 33 | 35 |
| 15 | 35 | 35 |
| 20 | 35 | 35 |
| 25 | 35 | 35 |

Surprisingly, the in-vivo measurement indicated absence of dilution and thus shows the ability of the double layered capnoxygen mask to provide high quality $CO_2$ monitoring alongside oxygen delivery.

Figure 11:
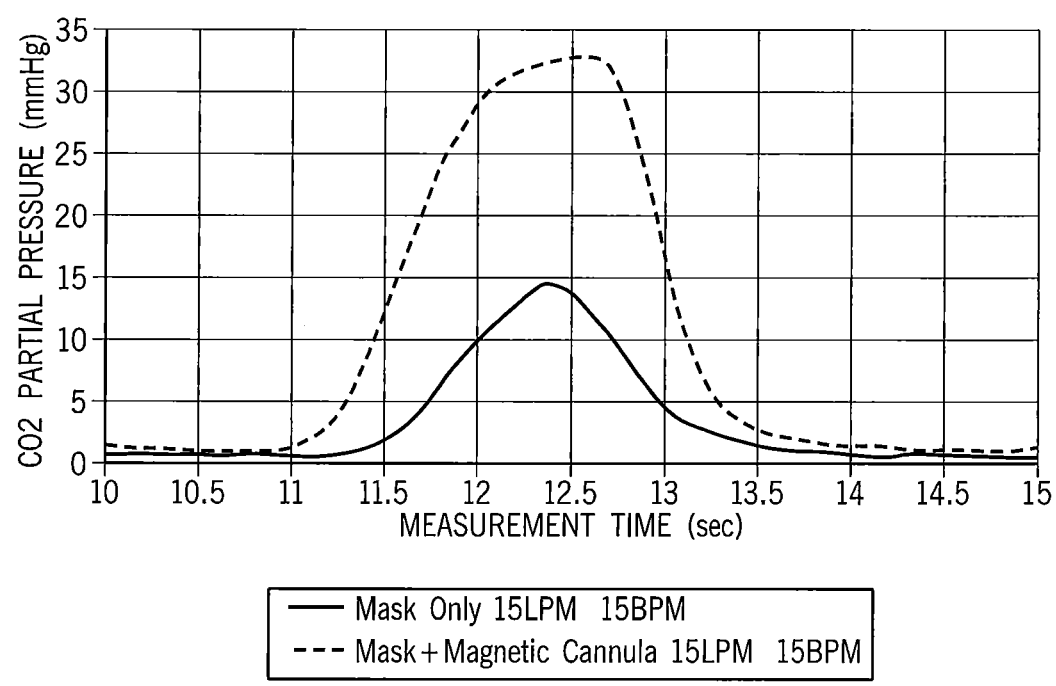
FIG. 11 shows the $CO_2$ waveforms obtained when evaluating a standard oxygen mask alone or in conjunction with the breath sampling cannula depicted in FIG. 5A and FIG. 5B.

Standard Oxygen Mask in Conjunction with Breath Sampling Cannula with Magnets $CO_2$ waveforms were also measured using a standard oxygen mask alone or in conjunction with the breath sampling cannula with magnets, depicted in FIG. 5A and FIG. 5B. The test was performed at oxygen flows of 5 LPM and 15 LPM and showed reduced dilution and satisfying waveform shape, as seen in FIG. 11.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present techniques may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but not limited to, any type of disk, including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions, as described herein.

The techniques may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. An oxygen mask configured for $CO_2$ sampling and oxygen delivery, the oxygen mask comprising:
   an oxygen inlet,
   a nasal breath-sampling element configured to reduce dilution of exhaled breath by the delivered oxygen, wherein the nasal breath-sampling element comprises an inner sampling compartment, wherein the oxygen mask comprises an inner wall separating the oxygen mask into the inner sampling compartment and an outer oxygen delivery compartment and wherein the inner wall comprises a plurality of oxygen supply perforations through which oxygen can reach the inner sampling compartment; and
   a breath sampling port configured to receive breath samples, sampled by the breath sampling element.

2. The oxygen mask of claim 1, wherein the nasal breath-sampling element is molded on, or otherwise attached to, an internal side of the oxygen mask.

3. The oxygen mask of claim 1, further comprising an oral sampling element configured for sampling exhaled breath from a subject's mouth when in use.

4. The oxygen mask of claim 1, wherein the nasal breath-sampling element comprises two nasal prongs fitted within the mask so as to be positioned within or below a subject's nostrils when in use.

5. The oxygen mask of claim 4, wherein the two nasal prongs are connected to an adjustment handle, the adjustment handle located outside the oxygen mask, wherein movement of the adjustment handle enables adjusting a position of the two nasal prongs within the oxygen mask.

6. The oxygen mask of claim 1, wherein the inner sampling compartment comprises two nasal prongs fitted within the inner sampling compartment so as to be positioned within or below a subject's nostrils, when in use.

7. The oxygen mask of claim 1, further comprising a breath sampling tube attached to the breath sampling port.

* * * * *